(12) United States Patent
Nawamaki et al.

(10) Patent No.: US 6,562,756 B1
(45) Date of Patent: May 13, 2003

(54) HERBICIDAL COMPOSITIONS

(75) Inventors: Tsutomu Nawamaki, Tokyo (JP); Shigeomi Watanabe, Shiraoka-machi (JP); Kunimitsu Nakahira, Shiraoka-machi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 10/070,897

(22) PCT Filed: Sep. 5, 2000

(86) PCT No.: PCT/JP00/06016

§ 371 (c)(1),
(2), (4) Date: Mar. 13, 2002

(87) PCT Pub. No.: WO01/19188

PCT Pub. Date: Mar. 22, 2001

(30) Foreign Application Priority Data

Sep. 13, 1999 (JP) ............................................. 11/258720

(51) Int. Cl.⁷ .......................... A01N 25/32; A01N 43/54

(52) U.S. Cl. ......................... 504/105; 504/107; 504/136

(58) Field of Search ................................ 504/105, 107, 504/136

(56) References Cited

FOREIGN PATENT DOCUMENTS

| DE | 44 31 219 | | 3/1996 |
|---|---|---|---|
| DE | 195 06 202 | | 8/1996 |
| DE | 199 58 381 | * | 6/2001 |
| EP | 0 563 384 | | 10/1993 |
| WO | 98 47904 | | 10/1998 |

* cited by examiner

*Primary Examiner*—S. Mark Clardy
(74) *Attorney, Agent, or Firm*—Oblon, Spivak, McClelland, Maier & Neustadt, P.C.

(57) ABSTRACT

There are provided a novel herbicidal composition and method for controlling weeds, the composition comprising the uracil herbicide of Compound A wherein:
- $R^1$ represents hydrogen or halogen;
- $R^2$ represents halogen or cyano;
- $R^3$ represents $C_{1-4}$ alkyl;
- $R^4$ represents hydrogen, $C_{1-5}$ acyl, or benzoyl which may be substituted with $R^5$ which represents one to five substituents selected from the group consisting of halogen, $C_{1-4}$ alkyl, and $C_{1-4}$ alkoxy, and at least one compound selected from the group consisting of flurilazole (Compound B), diclonon (Compound C), MON 4660 (Compound D), and benoxacor (Compound E):

2 Claims, No Drawings

HERBICIDAL COMPOSITIONS

This application has been filed under 35 USC 371 as the national stage of international application PCT/JP 00/06016, filed Sep. 5, 2000.

FIELD OF THE INVENTION

This invention relates to a herbicidal composition having a reduced phytotoxicity against crops, in particular against maize, and a method for controlling weeds.

BACKGROUND OF THE INVENTION

A number of compounds have come into practical use as a herbicide for maize. No existing herbicides, however, satisfactorily meet the request to selectively control only target weeds without causing any phytotoxicity to maize.

Compound (A) of the following formula:

(A)

wherein $R^1$ represents hydrogen or halogen; $R^2$ represents halogen or cyano; $R^3$ represents $C_{1-4}$ alkyl; $R^4$ represents hydrogen, $C_{1-5}$ acyl, or benzoyl which may be substituted with $R^5$; and $R^5$ represents one to five substituents selected from the group consisting of halogen, $C_{1-4}$ alkyl and $C_{1-4}$ alkoxy, which is disclosed in JP-A-3-204865 and JP-A-5-186436, can provide more excellent herbicidal activities by both foliage treatment and soil treatment at a lower dose as compared with conventional herbicides, and can show good safety against crops, such as soybean and maize, by soil treatment. When applied by soil treatment to maize sown at a shallow sowing depth, however, Compound (A) may cause phytotoxicity to the maize.

Compound (B), Compound (C), Compound (D) and Compound (E) represented by the following formulae:

(B)

(C)

(D)

(E)

have come into practical use or are under development as a safener for sorghum, maize, wheat and the like against herbicides to be applied. However, no activities of said compounds to reduce phytotoxicity to maize caused by Compound (A) have been reported.

SUMMARY OF THE INVENTION

The present invention relates to the herbicidal compositions described in the following item [1] and item [2] (hereinafter, referred to as the composition of the present invention) and to the method for controlling weeds described in the following item [3] and item [4] (hereinafter, referred to as the method of the present invention).

[1] A herbicidal composition comprising Compound (A) of the following formula:

(A)

wherein $R^1$ represents hydrogen or halogen;

$R^2$ represents halogen or cyano;

$R^3$ represents $C_{1-4}$ alkyl;

$R^4$ represents hydrogen, $C_{1-5}$ acyl, or benzoyl which may be substituted with $R^5$; and $R^5$ represents one to five substituents selected from the group consisting of halogen, $C_{1-4}$ alkyl and $C_{1-4}$ alkoxy, and at least one compound selected from the group consisting of Compound (B), Compound (C), Compound (D) and Compound (E) represented by the following formulae:

(B)

-continued

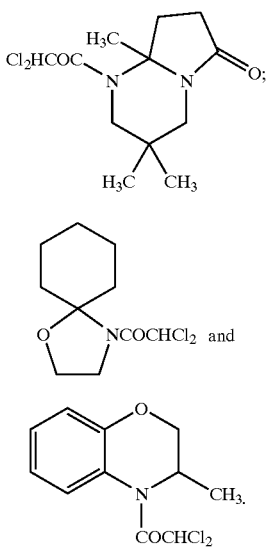

[2] A herbicidal composition for maize comprising Compound (A) mentioned in the above item [1] and at least one compound selected from the group consisting of Compound (B), Compound (C), Compound (D) and Compound (E) mentioned in the above item [1].

[3] A method for controlling weeds comprising applying Compound (A) mentioned in the above item [1] and at least one compound selected from the group consisting of Compound (B), Compound (C), Compound (D) and Compound (E) mentioned in the above item [1].

[4] A method for controlling weeds in a corn field comprising applying Compound (A) mentioned in the above item [1] and at least one compound selected from the group consisting of Compound (B), Compound (C), Compound (D) and Compound (E) mentioned in the above item [1].

According to the present invention, phytotoxicity to crops, in particular to maize, caused by the herbicidally active ingredient, Compound (A), is reduced by Compound (B), Compound (C), Compound (D) and/or Compound (E), while the herbicidal activities of Compound (A) against a variety of weeds are not decreased. Therefore, the present invention has a remarkably high practical usefulness.

DETAILED DESCRIPTION OF THE PRFERRED EMBODIMENTS

In Compound (A) to be used according to the present invention, $R^1$ may be hydrogen, fluorine, chlorine, bromine or iodine.

$R^2$ may be fluorine, chlorine, bromine, iodine or cyano.

$R^3$ may be methyl, ethyl, propyl, isopropyl, butyl, sec-butyl or tert-butyl.

$R^4$ may be hydrogen, formyl, acetyl, propionyl, butyryl, isobutyryl, valeryl, isovaleryl, pivaloyl, or benzoyl which may be substituted with $R^5$.

$R^5$ may be fluorine, chlorine, bromine, iodine, methyl, ethyl, propyl, isopropyl, butyl, sec-butyl, tert-butyl, methoxy, ethoxy, propoxy, isopropoxy, butoxy, sec-butoxy or tert-butoxy.

Preferred compounds within the scope of Compound (A) are the following. The abbreviations used have the following meanings.

H: hydrogen; F: fluorine; Cl: chlorine; Et: ethyl; Me: methyl; CN: cyano; COBut: pivaloyl; COPhOMe-4: 4-methoxybenzoyl Compound (A1): wherein $R^1$=F, $R^2$=Cl, $R^3$=Et, and $R^4$=H;
Compound (A2): wherein $R^1$=F, $R^2$=CN, $R^3$=Me, and $R^4$=H;
Compound (A3): wherein $R^1$=F, $R^2$=CN, $R^3$=Et, and $R^4$=COBut;
Compound (A4): wherein $R^1$=F, $R^2$=Cl, $R^3$=Et, and $R^4$=COPhOMe-4.

The preferred combinations of Compound (A) with at least one compound selected from the group consisting of Compound (B), Compound (C), Compound (D) and Compound (E) may be: Compound (A1)/Compound (B); Compound (A1)/Compound (C); Compound (A1)/Compound (D); Compound (A1)/Compound (E); Compound (A2)/Compound (B); Compound (A2)/Compound (C); Compound (A2)/Compound (D); Compound (A2)/Compound (E); Compound (A3)/Compound (B); Compound (A3)/Compound (C); Compound (A3)/Compound (D); Compound (A3)/Compound (E); Compound (A4)/Compound (B); Compound (A4)/Compound (C); Compound (A4)/Compound (D); and Compound (A4)/Compound (E).

According to the present invention, with respect to one part by weight of Compound (A), at least one compound selected from the group consisting of Compound (B), Compound (C), Compound (D) and Compound (E) is commonly applied in an amount of 0.001–100 parts by weight, preferably 0.01–10 parts by weight.

The application rate of Compound (A) is commonly 0.01–10 kg/ha, preferably 0.03–3 kg/ha. The application rate of at least one compound selected from the group consisting of Compound (B), Compound (C), Compound (D) and Compound (E) is commonly 0.001–10 kg/ha, preferably 0.003–3 kg/ha.

According to the present invention, Compound (A) and at least one compound selected the group consisting of Compound (B), Compound (C), Compound (D) and Compound (E) may be separately applied or may be applied as a mixed composition. When separately applied, they may be simultaneously applied or may be successively applied at a short time interval. All the above applying manners are included within the present invention.

For practical application, the composition of the present invention may be generally applied in an appropriate formulation such as soluble concentrate, emulsifiable concentrate, wettable powder, water soluble powder, water dispersible granule, water soluble granule, suspension concentrate, concentrated emulsion, suspoemulsion, microemulsion, dustable powder, granule and gel, which may be prepared by combining the composition with appropriate solid or liquid carriers, and optionally with appropriate additives such as surfactants, penetrating agents, spreaders, thickeners, antifreezing agents, binders, anticaking agents, disintegrators, antifoaming agents, preservatives and stabilizers. In addition, for labor saving and improvement in safety, any of the above formulations may be encapsulated in water-soluble capsules and then applied. They may be, as necessary, subjected to a combined application with one or more other herbicides, insecticides, fungicides, plant growth regulators, fertilizers and the like by mixing them during formulating process or on applying them.

In particular, the combined application of the present composition with one or more other herbicides can widen the herbicidal spectrum and can make more stable the effect achieved by the present invention.

The solid carriers include natural mineral materials such as quartz, kaolinite, pyrophyllite, sericite, talc, bentonite, acid clay, attapulgite, zeolite and diatomaceous earth; inorganic salts such as calcium carbonate, ammonium sulfate, sodium sulfate and potassium chloride; synthetic silica; and synthetic silicate.

The liquid carriers include alcohols such as ethylene glycol, propylene glycol and isopropanol; aromatic hydrocarbons such as xylenes, alkylbenzenes and alkylnaphthalenes; ethers such as butyl cellosolve; ketones such as cyclohexanone; esters such as γ-butyrolactone; acid amides such as N-methylpyrrolidone and N-octylpyrrolidone; vegetable oils such as soybean oil, rape seed oil, cottonseed oil and castor oil; and water.

These solid and liquid carriers may be used alone or in combination of two or more.

The surfactants include nonionic surfactants such as polyoxyethylene alkyl ethers, polyoxyethylene alkylaryl ethers, polyoxyethylene styrylphenyl ethers, polyoxyethylene-polyoxypropylene block copolymer, polyoxyethylene aliphatic acid esters, sorbitan aliphatic acid esters and polyoxyethylenesorbitan aliphatic acid esters; anionic surfactants such as alkylsulfate salts, alkylbenzenesulfonate salts, lignosulfonate salts, alkylsulfosuccinate salts, naphthalenesulfonate salts, alkylnaphthalenesulfonate salts, salts of formalin condensation product with naphthalenesulfonic acid, salts of formalin condensation product with alkylnaphthalenesulfonic acid, polyoxyethylene alkylaryl ether sulfate and phosphate salts, polyoxyethylene styrylphenyl ether sulfate and phosphate salts, polycarboxylate salts and polystyrenesulfonate salts; cationic surfactants such as alkylamine salts and alkyl quaternary ammonium salts; and amino-acid type and betaine type of ampholytic surfactants.

The total amount of these surfactants is desirably, but not limited to, 0.05 to 20 parts by weight with respect to 100 parts by weight of a formulation of this invention. These surfactants may be used alone or in combination of two or more.

Formulation examples for the composition of the present invention are shown below, but this invention is not limited to the specific formulations. In the following examples, the term "part (or parts)" means part (or parts) by weight.

[Wettable powder]

|  | parts |
|---|---|
| Compound (A) + Compound (B) | 5–80 |
| Solid carrier | 10–85 |
| Surfactant | 1–10 |
| Others | 1-5 |

(Others include anticaking agent and the like.)

[Emulsifiable concentrate]

|  | parts |
|---|---|
| Compound (A) + Compound (B) | 1–30 |
| Liquid carrier | 30–95 |
| Surfactant | 4–15 |
| Others | 0–25 |

(Others include spreader and stabilizer and the like.)

[Suspension concentrate]

|  | parts |
|---|---|
| Compound (A) + Compound (B) | 5–70 |
| Liquid carrier | 15–65 |
| Surfactant | 5–12 |
| Others | 5–30 |

(Others include anti-freezing agent and thickner and the like.)

[Water dispersible granule]

|  | parts |
|---|---|
| Compound (A) + Compound (B) | 0.1–90 |
| Solid carrier | 0–98.9 |
| Surfactant | 1–20 |
| Others | 0–10 |

(Others include binder and stabilizer and the like.)

Specific herbicidal composition of the present invention will be illustrated below, but the present invention is not limited to the specific examples. In the following examples, the term "part (or parts)" means part (or parts) by weight.

Formulation Example 1 : Suspension concentrate

|  | parts |
|---|---|
| Compound (A4) | 12 |
| Compound (B) | 12 |
| Agrisol S-711 (trademark) | 8 |
| (nonionic surfactant: Kao Co.) | |
| Runox 1000C (trademark) | 0.5 |
| (anionic surfactant: Toho Chemical Ind. Co., Ltd.) | |
| Xanthan gum | 0.2 |
| Ethylene glycol | 8 |
| (anti-freezing agent) | |
| Water | 59.3 |

These ingredients are homogeneously blended and then wet-ground to provide a suspension concentrate.

Formulation Example 2 : Suspension concentrate

|  | parts |
|---|---|
| Compound (A4) | 12 |
| Compound (C) | 12 |
| Agrisol S-711 (trademark) | 8 |
| (nonionic surfactant: Kao Co.) | |
| Runox 1000C (trademark) | 0.5 |
| (anionic surfactant: Toho Chemical Ind. Co., Ltd.) | |
| Xanthan gum | 0.2 |
| Ethylene glycol | 8 |
| (anti-freezing agent) | |
| Water | 59.3 |

These ingredients are homogeneously blended and then wet-ground to provide a suspension concentrate.

Formulation Example 3 : Suspension concentrate

| | parts |
|---|---|
| Compound (A4) | 12 |
| Compound (D) | 12 |
| Agrisol S-711 (trademark) | 8 |
| (nonionic surfactant: Kao Co.) | |
| Runox 1000C (trademark) | 0.5 |
| (anionic surfactant: Toho Chemical Ind. Co., Ltd.) | |
| Xanthan gum | 0.2 |
| Ethylene glycol | 8 |
| (anti-freezing agent) | |
| Water | 59.3 |

These ingredients are homogeneously blended and then wet-ground to provide a suspension concentrate.

Formulation Example 4 : Suspension concentrate

| | parts |
|---|---|
| Compound (A4) | 12 |
| Compound (E) | 12 |
| Agrisol S-711 (trademark) | 8 |
| (nonionic surfactant: Kao Co.) | |
| Runox 1000C (trademark) | 0.5 |
| (anionic surfactant: Toho Chemical Ind. Co., Ltd.) | |
| Xanthan gum | 0.2 |
| Ethylene glycol | 8 |
| (anti-freezing agent) | |
| Water | 59.3 |

These ingredients are homogeneously blended and then wet-ground to provide a suspension concentrate.

Formulation Example 5 : Water dispersible granule

| | parts |
|---|---|
| Compound (A4) | 30 |
| Compound (B) | 30 |
| Hitenol NE-15 (trademark) | 10 |
| (anionic surfactant: Dai-Ichi Kogyo Seiyaku Co., Ltd.) | |
| Vanilex N (trademark) | 10 |
| (anionic surfactant: Nippon Paper Ind. Co., Ltd.) | |
| Carplex #80D (trademark) | 10 |
| (synthetic hydrous silica: Shionogi & Co., Ltd.) | |
| Pyrophyllite | 10 |

These ingredients are homogeneously blended, ground, kneaded with a small amount of water with stirring, granulated with an extrusion granulator and then dried to provide a water dispersible granule.

Formulation Example 6 : Water dispersible granule

| | parts |
|---|---|
| Compound (A4) | 30 |
| Compound (C) | 30 |
| Hitenol NE-15 (trademark) | 10 |
| (anionic surfactant: Dai-Ichi Kogyo Seiyaku Co., Ltd.) | |
| Vanilex N (trademark) | 10 |
| (anionic surfactant: Nippon Paper Ind. Co., Ltd.) | |
| Carplex #80D (trademark) | 10 |
| (synthetic hydrous silica: Shionogi & Co., Ltd.) | |
| Pyrophyllite | 10 |

These ingredients are homogeneously blended, ground, kneaded with a small amount of water with stirring, granulated with an extrusion granulator and then dried to provide a water dispersible granule.

Formulation Example 7 : Water dispersible granule

| | parts |
|---|---|
| Compound (A4) | 30 |
| Compound (E) | 30 |
| Hitenol NE-15 (trademark) | 10 |
| (anionic surfactant: Dai-Ichi Kogyo Seiyaku Co., Ltd.) | |
| Vanilex N (trademark) | 10 |
| (anionic surfactant: Nippon Paper Ind. Co., Ltd.) | |
| Carplex #80D (trademark) | 10 |
| (synthetic hydrous silica: Shionogi & Co., Ltd.) | |
| Pyrophyllite | 10 |

These ingredients are homogeneously blended, ground, kneaded with a small amount of water with stirring, granulated with an extrusion granulator and then dried to provide a water dispersible granule.

Formulation Example 8 : Wettable powder

| | parts |
|---|---|
| Compound (A4) | 30 |
| Compound (B) | 30 |
| Pyrophyllite | 34 |
| Sorpol 5039 (trademark) | 4 |
| (mixture of nonionic and anionic surfactants: Toho Chemical Ind. Co., Ltd.) | |
| Carplex #80D (trademark) | 2 |
| (synthetic hydrous silica: Shionogi & Co., Ltd.) | |

These ingredients are homogeneously blended and ground to provide a wettable powder.

EXAMPLE

The following Test Examples specifically show usefulness of the composition of the present invention as a herbicide.

Test Example 1

Test on Phytotoxicity to Maize Sown at a Shallow Sowing Depth

Cylindrical pots having an inner diameter of about 11 cm and a depth of 10 cm were charged with sterilized upland soil. In each pot, three seeds of maize were separately seeded at a sowing depth of 1 cm. On the day of seeding, wettable powder appropriately formulated according to the above Formulation Examples was diluted with water and then applied with a small type sprayer at a spray volume of 10 liter/are. Seventeen days after the application, the fresh weight of aerial parts of each plant was determined and then compared with those of untreated plants. The results are shown in Table 1.

TABLE 1

| Compound | Application rate of active ingredients (g/ha) | Fresh weight ratio with respect to untreated plants (%) |
|---|---|---|
| Compound (A1) | 40 | 70 |
|  | 80 | 55 |
| Compound (A1) + Compound (B) | 40 + 40 | 99 |
|  | 80 + 80 | 87 |
| Compound (A1) + Compound (C) | 40 + 40 | 92 |
|  | 80 + 80 | 85 |
| Compound (A1) + Compound (D) | 40 + 40 | 94 |
|  | 80 + 80 | 88 |
| Compound (A1) + Compound (E) | 40 + 40 | 98 |
|  | 80 + 80 | 90 |
| Compound (A2) | 40 | 90 |
|  | 80 | 76 |
| Compound (A2) + Compound (B) | 40 + 40 | 100 |
|  | 80 + 80 | 100 |
| Compound (A2) + Compound (C) | 40 + 40 | 100 |
|  | 80 + 80 | 100 |
| Compound (A2) + Compound (D) | 40 + 40 | 100 |
|  | 80 + 80 | 100 |
| Compound (A2) + Compound (E) | 40 + 40 | 100 |
|  | 80 + 80 | 100 |
| Compound (A3) | 40 | 84 |
|  | 80 | 60 |
| Compound (A3) + Compound (B) | 40 + 40 | 100 |
|  | 80 + 80 | 100 |
| Compound (A3) + Compound (C) | 40 + 40 | 100 |
|  | 80 + 80 | 98 |
| Compound (A3) + Compound (D) | 40 + 40 | 100 |
|  | 80 + 80 | 97 |
| Compound (A3) + Compound (E) | 40 + 40 | 100 |
|  | 80 + 80 | 98 |
| Compound (A4) | 40 | 73 |
|  | 80 | 57 |
| Compound (A4) + Compound (B) | 40 + 40 | 100 |
|  | 80 + 80 | 92 |
| Compound (A4) + Compound (C) | 40 + 40 | 100 |
|  | 80 + 80 | 89 |
| Compound (A4) + Compound (D) | 40 + 40 | 92 |
|  | 80 + 80 | 88 |
| Compound (A4) + Compound (E) | 40 + 40 | 100 |
|  | 80 + 80 | 90 |
| Compound (B) | 40 | 100 |
|  | 80 | 100 |
| Compound (C) | 40 | 100 |
|  | 80 | 100 |
| Compound (D) | 40 | 100 |
|  | 80 | 100 |
| Compound (E) | 40 | 100 |
|  | 80 | 100 |

Test Example 2

Test on Herbicidal Effects by Soil Treatment

Plastic cases having a size of 30 cm (length), 30 cm (width) and 10 cm (depth) were charged with sterilized upland soil. In each plastic case, seeds of velvetleaf (*Abutilon theophrasti*), common lambsquarters (*Chenopodium album*), redroot pigweed (*Amaranthus viridis*) and common ragweed (*Ambrosia artemisiaefolia*) were seeded, and covered with soil of 0.5 cm thickness. On the day of seeding, wettable powder appropriately formulated according to the above Formulation Examples was diluted with water and then applied with a small type sprayer at a spray volume of 10 liter/are. Four weeks after the application, the fresh weight of aerial parts of each weed was determined and then compared with those of untreated weed. The results are shown in Table 2.

TABLE 2

| Compound | Application rate of active ingredients (g/ha) | Fresh weight ratio with respect to untreated weeds (%) | | | |
|---|---|---|---|---|---|
| | | A.th | C.al | A.vi | A.ar |
| Comp. (A1) | 5 | 26 | 13 | 5 | 31 |
|  | 10 | 2 | 0 | 0 | 7 |
| Comp. (A1) + Comp. (B) | 5 + 5 | 30 | 16 | 5 | 33 |
|  | 10 + 10 | 4 | 0 | 0 | 6 |
| Comp. (A1) + Comp. (C) | 5 + 5 | 24 | 15 | 7 | 32 |
|  | 10 + 10 | 0 | 0 | 0 | 3 |
| Comp. (A1) + Comp. (D) | 5 + 5 | 27 | 13 | 2 | 37 |
|  | 10 + 10 | 2 | 0 | 0 | 3 |
| Comp. (A1) + Comp. (E) | 5 + 5 | 27 | 17 | 7 | 30 |
|  | 10 + 10 | 2 | 0 | 0 | 5 |
| Comp. (A2) | 5 | 32 | 18 | 9 | 40 |
|  | 10 | 4 | 0 | 0 | 10 |
| Comp. (A2) + Comp. (B) | 5 + 5 | 33 | 19 | 6 | 42 |
|  | 10 + 10 | 5 | 0 | 0 | 9 |
| Comp. (A2) + Comp. (C) | 5 + 5 | 36 | 18 | 8 | 43 |
|  | 10 + 10 | 4 | 0 | 0 | 11 |
| Comp. (A2) + Comp. (D) | 5 + 5 | 33 | 20 | 5 | 45 |
|  | 10 + 10 | 6 | 0 | 0 | 10 |
| Comp. (A2) + Comp. (E) | 5 + 5 | 32 | 19 | 7 | 42 |
|  | 10 + 10 | 5 | 0 | 0 | 11 |
| Comp. (A3) | 5 | 24 | 15 | 6 | 37 |
|  | 10 | 1 | 0 | 0 | 11 |
| Comp. (A3) + Comp. (B) | 5 + 5 | 25 | 18 | 6 | 39 |
|  | 10 + 10 | 0 | 0 | 0 | 12 |
| Comp. (A3) + Comp. (C) | 5 + 5 | 27 | 19 | 8 | 39 |
|  | 10 + 10 | 3 | 0 | 0 | 11 |
| Comp. (A3) + Comp. (D) | 5 + 5 | 29 | 19 | 8 | 40 |
|  | 10 + 10 | 3 | 2 | 0 | 14 |
| Comp. (A3) + Comp. (E) | 5 + 5 | 25 | 16 | 7 | 38 |
|  | 10 + 10 | 1 | 0 | 0 | 12 |
| Comp. (A4) | 5 | 27 | 17 | 9 | 40 |
|  | 10 | 5 | 0 | 0 | 14 |
| Comp. (A4) + Comp. (B) | 5 + 5 | 28 | 18 | 10 | 41 |
|  | 10 + 10 | 5 | 0 | 0 | 15 |
| Comp. (A4) + Comp. (C) | 5 + 5 | 29 | 19 | 12 | 44 |
|  | 10 + 10 | 5 | 0 | 0 | 17 |
| Comp. (A4) + Comp. (D) | 5 + 5 | 31 | 21 | 13 | 45 |
|  | 10 + 10 | 8 | 1 | 1 | 17 |
| Comp. (A4) + Comp. (E) | 5 + 5 | 28 | 18 | 11 | 41 |
|  | 10 + 10 | 6 | 0 | 0 | 14 |
| Comp. (B) | 5 | 100 | 100 | 100 | 100 |
|  | 10 | 100 | 100 | 100 | 100 |
| Comp. (C) | 5 | 100 | 100 | 100 | 100 |
|  | 10 | 100 | 100 | 100 | 100 |
| Comp. (D) | 5 | 100 | 100 | 100 | 100 |
|  | 10 | 100 | 100 | 100 | 100 |
| Comp. (E) | 5 | 100 | 100 | 100 | 100 |
|  | 10 | 100 | 100 | 100 | 100 |

(A.th: *Abutilon theophrasti*; C.al: *Chenopodium album*; A.vi: *Amaranthus viridis*; A.ar: *Ambrosia artemisiaefolia*)

As seen from the above results, the phytotoxicities to maize sown at a shallow sowing depth which are caused by Compound (A1), Compound (A2), Compound (A3) or Compound (A4), are remarkably reduced by Compound (B), Compound (C), Compound (D) or Compound (E), while the herbicidal activities of Compound (A1), Compound (A2), Compound (A3) and Compound (A4) are not decreased.

What is claimed is:

1. A herbicidal composition comprising Compound (A) of the following formula:

(A) 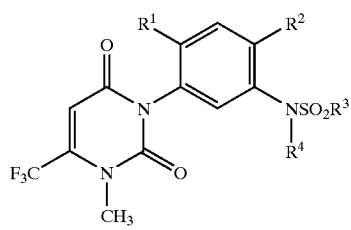

wherein
- $R^1$ represents hydrogen or halogen;
- $R^2$ represents halogen or cyano;
- $R^3$ represents $C_{1-4}$ alkyl;
- $R^4$ represents hydrogen, $C_{1-5}$ acyl, or benzoyl which may be substituted with $R^5$; and
- $R_5$ represents one to five substituents selected from the group consisting of halogen, $C_{1-4}$ alkyl and $C_{1-4}$ alkoxy, and at least one compound selected from the group consisting of Compound (B), Compound (C), Compound (D) and Compound (E) of the following formulae:

(B)

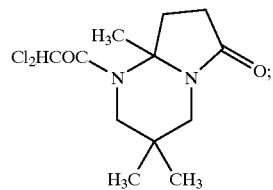

(C)

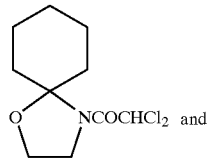

(D)

(E)

2. A method for controlling weeds comprising applying Compound (A) as defined in claim 1 and at least one compound selected from the group consisting of Compound (B), Compound (c), Compound (D) and Compound (E) as defined in claim 1.

* * * * *